United States Patent
Kim et al.

(10) Patent No.: US 10,575,920 B2
(45) Date of Patent: Mar. 3, 2020

(54) AUGMENTED REALITY IMAGE PROJECTION SYSTEM

(71) Applicant: NATIONAL CANCER CENTER, Goyang-si, Gyeonggi-do (KR)

(72) Inventors: Seok Ki Kim, Seoul (KR); Seong Cheon Kim, Goyang-si (KR); Sun Up Park, Seoul (KR)

(73) Assignee: NATIONAL CANCER CENTER (KR)

( * ) Notice: Subject to any disclaimer, the term of this patent is extended or adjusted under 35 U.S.C. 154(b) by 0 days.

(21) Appl. No.: 15/556,945

(22) PCT Filed: Feb. 1, 2016

(86) PCT No.: PCT/KR2016/001049
§ 371 (c)(1),
(2) Date: Sep. 8, 2017

(87) PCT Pub. No.: WO2016/144005
PCT Pub. Date: Sep. 15, 2016

(65) Prior Publication Data
US 2018/0042692 A1    Feb. 15, 2018

(30) Foreign Application Priority Data
Mar. 9, 2015   (KR) ................ 10-2015-0032371

(51) Int. Cl.
*A61B 90/00*   (2016.01)
*A61B 1/04*    (2006.01)
*A61B 1/313*   (2006.01)

(52) U.S. Cl.
CPC ........... *A61B 90/361* (2016.02); *A61B 1/043* (2013.01); *A61B 1/313* (2013.01); *A61B 90/36* (2016.02);
(Continued)

(58) Field of Classification Search
None
See application file for complete search history.

(56) References Cited

U.S. PATENT DOCUMENTS

2002/0082498 A1   6/2002   Wendt et al.
2005/0219552 A1 * 10/2005  Ackerman ............. A61B 1/042
                                                    356/603
(Continued)

FOREIGN PATENT DOCUMENTS

EP    0676902 A2 * 10/1995 ........... H04N 9/3152
KR    10-0686525 B1   2/2007
KR    10-0726028 B1   6/2007

OTHER PUBLICATIONS

Nicolau et al.: "Augmented Reality in Laparoscopic Surgical Oncology", Surgical Oncology, 2011, vol. 20, No. 3, pp. 189-201 (Abstract only).
(Continued)

*Primary Examiner* — YuJang Tswei
(74) *Attorney, Agent, or Firm* — Harness, Dickey & Pierce, P.L.C.

(57) ABSTRACT

The present disclosure relates to an augmented reality (AR) image projection system capable of simultaneously capturing a real image and projecting an AR image, and capable of applying same to a subject requiring precise work or in an environment having spatial restrictions. The present disclosure includes a real image capture device for capturing a real image illuminated by invisible rays without interference with visible rays, and an AR image projection device for projecting an AR image, wherein the real image capture device captures a real image and the AR image projection device projects an AR image through the same optical axis. Further, the present disclosure includes a real image capture device, an AR image projection device, as well as additional imaging devices such as a fluorescent camera configured
(Continued)

integrally along the same optical axis, and configured to avoid wavelength interference between a light source and an excitation light and the like.

14 Claims, 5 Drawing Sheets

(52) U.S. Cl.
CPC ........ *A61B 90/37* (2016.02); *A61B 2090/365* (2016.02); *A61B 2090/366* (2016.02)

(56) References Cited

U.S. PATENT DOCUMENTS

| | | | |
|---|---|---|---|
| 2011/0242308 A1* | 10/2011 | Igarashi | G01N 21/6458 348/79 |
| 2012/0007839 A1* | 1/2012 | Tsao | G02B 26/00 345/204 |
| 2014/0022283 A1 | 1/2014 | Chan et al. | |
| 2015/0061527 A1* | 3/2015 | Hamanaka | H02M 1/32 315/209 R |
| 2015/0153572 A1* | 6/2015 | Miao | G02B 27/017 345/8 |
| 2015/0205135 A1* | 7/2015 | Border | G02B 27/0172 359/630 |

OTHER PUBLICATIONS

International Search Report (in English and Korean) and Written Opinion (in Korean) of the International Searching Authority issued in PCT/KR2016/001049, dated Jul. 1, 2016 ISA/KR.

U.S. Appl. No. 15/553,858, filed Aug. 25, 2017, Kim, Seok Ki, et al.

\* cited by examiner

AUGMENTED REALITY IMAGE PROJECTION SYSTEM

CROSS-REFERENCE TO RELATED APPLICATION

The present application is the US national phase of International Patent Application No. PCT/KR2016/001049, filed Feb. 1, 2016, which claims priority to Korean Patent Application No. 10-2015-0032371, filed on Mar. 9, 2015. The disclosures of the above-listed applications are hereby incorporated by reference herein in their entirety.

TECHNICAL FIELD

The present disclosure in some embodiments relates to a technology for projecting an augmented reality (AR) image. More particularly, the present disclosure relates to an augmented reality projection system which is capable of simultaneously capturing the real image and projecting the augmented reality image, and is applicable to geometrically restricted spaces and/or to an object subject to a precision operation.

BACKGROUND

In general, augmented reality is a technology for showing computer generated graphics (virtual images) overlapped with a real image to make the viewer feel as if the computer generated graphics is in the real world. The AR technology aims to complement the real world with the virtual realm, and the majority of the augmented reality information resides in the real image that the human eyes see.

The computer-generated virtual image may contain a variety of graphical or non-imagery information such as text in registration with an object image besides the ordinary real image. Such computer-generated virtual image may be a marker image of an object with markers attached to include the object's positional information for aligning the virtual image with the real image, a stereo image containing three-dimensional geometric information of the scene to subsequently extract the coordinate data, or existing medical images such as CT, MRI, and PET. Other than the obtained images before the AR image registration, a special image (inclusive of a processed real image) generated in real time while capturing a real image may be used as a virtual image (computer image) for realizing the AR. The special image may be a fluorescent image which receives extensive attention from several fields. In particular, a near infrared (NIR) fluorescent image is widely used in the biomedical field. This wealth of information can be well applied simultaneously to construct a computer-generated virtual image.

The method to overlap virtual images onto the real image that the human eyes see is implemented by the usage of a semi-translucent display, augmented reality glasses, or a head-mount display (HMD).

An exact registration or alignment of the virtual image with the real image is required for realizing augmented reality. It is required to have the virtual image that spatially matches in alignment with the real image exactly to realize the augmented reality. Further, it is necessary to have the geometric information to responsibly align the virtual image onto the real image in the same space coordinate in real-time with the change in the distance or the orientation of the subject and the projector. In case of an HMD, three-dimensional computer graphics data is needed to provide an aligned virtual image projection onto the real image regardless of the distance or orientation with respect to the subject. In case of a semi-translucent display or augmented reality glasses, to render a subject behind the semi-translucent display or augmented reality glasses in registration with computer graphics on the relevant display, a computer-generated virtual image needs to be projected taking account of the observer's line of sight and the distance from the subject, which necessitates three-dimensional computer-generated virtual image information in spatial registration with the subject behind.

Providing viewing experience which is natural and accurate without discomfort or distortion of reality matters much in the augmented reality composed of the computer-generated virtual image and the real image. This applies especially to the AR system used in precise medical operations or hazardous works. For example, the AR system is not supposed to interfere with the delicate medical operation. However, an HMD or a semi-translucent screen is in between the operation site and the operator's eyes so it is prone to be contaminated and may cause a sense of visual discord by interfering with the line of sight partially.

The augmented reality system of some embodiments of the present disclosure directly projects and aligns the computer-generated virtual image onto the subject, unlike the method which uses a semi-translucent display for the virtual image projection including the registration of the projected virtual image with the image of the subject behind the semi-translucent display. Generating an AR image by casting (projecting) a virtual image directly on the subject may realize an augmented reality with less sense of discomfort in performing high-accuracy or high-risk operation because the observer is to see the actual subject.

A conventional AR system as depicted in FIGS. 4 and 5 needs to be comprised of a device to generate computer-generated virtual image including data to be added to the real image; a (real-virtual image alignment) device for aligning (calculating and transforming) the coordinates of the computer-generated virtual image to that of the real image; and a projection device of the AR image which contains the real image overlapped with the computer-generated virtual image.

Augmented reality image projection system, which projects an image to the subject, needs a projection device further to a typical AR system. As a real image capture device and the projection device may not be in alignment, a device (alignment device for aligning the computer-generated virtual image to the subject) is additionally necessary for aligning the subject and the computer-generated virtual image.

However, a conventional augmented reality image projection system, which is a side-by-side arrangement of two dedicated units of a projection device and a real image capture device, has following issues.

First, it involves a complicated process of aligning the projection onto the subject. The lack of unity between the projection device for projecting the AR image and the real image capture device which serves as an alignment reference results in their discrepancies in direction and distance. The AR image cannot be projected as it is, and needs an alignment process for registration with the subject. For the alignment registration, a special algorithm may be used to compare and match the captured subject image and the AR image in real time. A method using a sort of markers or stereoscopic cameras may also be used as described in Korean Patent Publication No. 10-0726028 (May 31, 2007). Such markers or stereoscopic cameras provide the positional information of the subject as a tracker. The information provided by the tracker is fed to the system to align the AR image with the subject by adjusting the size, position, or angle of orientation. Such projection system may still have discomfort for the viewer as there may exist a time delay in the projected image. It takes a lot of calculations to get an image for projection if there is a real-time change of distance or direction between the subject and the projection system, or the subject is expected to move relentlessly. In addition, as the subject is three-dimensional having a certain thickness, the distance of the subject from the projection system differs portion by portion, which requires an additional calculation time for alignment even if a stereoscopic camera is in use. A fundamental shortcoming is shown in FIG. 5 that the projection system has blind spots where the projection system cannot reach due to an angular difference between the line of sight and the line of projection.

Second, a size of the system is hard to be reduced in compact form if each device is configured independently. As the separately installed camera and projection device may occupy a large space, 1) it may block the line of sight of the observer who needs to see an AR image projected onto the subject, which limits the usability of the system. Size reduction of the AR image projection system is not feasible in typical projection system having separate devices for projecting and imaging including positional information. Such cases include 2) when an endoscopic or a laparoscopic device is in use to view the subject, or 3) when the system is to be configured in places like an astral lamp. The size of the system can play a decisive role in particular applications.

Third, it is technically difficult to implement additional real-time imaging device such as a fluorescence imaging device. Additional imaging device requires additional trackers or complicated calculation for image alignment. Physical realization is hard as additional devices are necessary according to the additional number of images. For example, devices for capturing a thermal image of the subject and then projecting, or capturing a fluorescent image of the subject and then projecting may be added side by side to a subject image capture device and a projection device. It becomes very complicated system occupying a lot of space.

Fourth, interference between the projection image and the illumination of the subject diminishes the contrast of projected AR image. Additional fluorescence image further makes it difficult to configure the system as it interferes with the excitation light source.

Illumination is always necessary for both the conventional augmented reality image projection system or the augmented reality image projection system of the present disclosure as both need to take a real image for alignment. The real image serves as a basis for alignment in augmented reality image. In general, the wavelength range of illumination for capturing the real image and that of the projected image from the augmented reality image projection system overlap. In this case, increasing the intensity of the illumination to improve the captured image quality 1) makes the projected image less visible and 2) results in an adverse effect on alignment as the projection image is taken together with the real image. Such interference necessitates a sophisticated device for separately controlling the illuminating device to project a good contrast image. Such device includes a complicated method using time-division illumination and toggling between illumination and image projection to prevent such interference. However, this approach makes the system complex and also brings serious inconvenience to the user's view due to the flashing illumination. 3) In case a fluorescent image is appended, an additional time division is required as the white light illumination interferes with the excitation illumination which prevents simultaneous acquisition and projection of the images.

Placing wavelength range of the illumination for the real image in invisible light range (in particular, infrared range) can fundamentally solve the interference issue of the projected computer-generated AR image and the excitation source for the fluorescence without a complicated time-division scheme. Especially for the AR image projection system according to some embodiments of the present disclosure, real image taken by illuminating with invisible light source suits better as its primary purpose is for image alignment. Previous AR projection system is unable to solve the interference issue between illumination, projection image, and special imaging. Such interference is a problem needed to be solved to build a practical working system.

DISCLOSURE

Technical Problem

The present disclosure in some embodiments seeks to solve the conventional deficiencies as described above. The AR image projection system according to some embodiments of the present disclosure seeks to provide a simple and compact system by configuring both the augmented reality image projection device and the real image capture device to have the same optical axis.

The present disclosure in some embodiments further seeks to provide illumination for the real image capture device with invisible light to prevent the interference and to provide a contrasty AR image.

The present disclosure in some embodiments further seeks to provide a variety of AR images by applying multiples of the fluorescent image capture device.

The present disclosure in some embodiments further seeks to provide a compact system with unified imaging and projecting devices for a narrow and confined operational site so that it may be integrated into devices such as a laparoscope, thoracoscope, cystoscope, or exoscope.

The present disclosure in some embodiments further seeks to develop a compact system which does not intervene the movement of the operator so that it may readily be applied to a surgical operation that needs direct, unobstructed manipulation at the site.

The present disclosure in some embodiments further seeks to provide a compact system which may be integrated singly or in multiples into another equipment such as an astral lamp.

SUMMARY

The augmented reality image projection system according to some embodiments of the present disclosure is configured in such ways that an alignment device for aligning the subject to the computer-generated virtual image is added to the conventional augmented reality system. It is also configured in a unified arrangement to provide effective and efficient image alignment, reducing the interference between the projection and imaging.

The augmented reality image projection system according to some embodiments of the present disclosure includes a real image capture device configured to take a real image of a subject, and an augmented reality image projection device configured to project an augmented reality image onto the subject. Here, the real image capture device captures the real image and the augmented reality image projection device projects the augmented reality image along the same optical axis.

Further, the augmented reality image projection system according to some embodiments of the present disclosure includes a first dichroic mirror configured to be disposed between the augmented reality image projection device and a projection lens, and to totally reflect the visible light while passing light having a wavelength longer than the visible light.

Further, the augmented reality image projection system according some embodiments of the present disclosure includes, as the real image capture device, an IR (infrared) real image capture device capable of capturing an infrared image, and the augmented reality image projection system includes an IR real image illumination source which provides infrared light for the IR real image capture device to capture the real image. The augmented reality image projection system may further include a beam splitter configured to distribute the infrared light provided by the IR real image illumination source by 50:50 ratio, and to reflect and transmit the distributed infrared light.

Further, the augmented reality image projection system according to some embodiments of the present disclosure arranges the real image capture device and the augmented reality image projection device to share the same optical axis, and the augmented reality image projection system may further include a fluorescent camera configured to take a fluorescent image.

Further, the augmented reality image projection system according to some embodiments of the present disclosure includes a fluorescent excitation light source configured to provide the excitation light for the fluorescent camera to take the fluorescent image.

Further, the augmented reality image projection system according to some embodiments of the present disclosure is integrated into an astral lamp, or into an eyepiece of a rigid endoscope such as a laparoscope, a thoracoscope, or a cystoscope to enhance the usability.

Further, the augmented reality image projection system according to some embodiments of the present disclosure has a compact form factor and may be placed near the front or side of the operator so that the operator may use it as an aid in various operations.

Advantageous Effects

The augmented reality image projection system according to some embodiments can provide a simple and compact system by making both the augmented reality image projection device and the real image capturing device to share the same optical axis. It eliminates or minimizes the use of an additional alignment device for aligning the augmented reality image to the subject or alignment device for aligning the computer-generated virtual image to the real image.

Further, multiple real-time imaging can be added as the projection device and the imaging device are located on the same optical axis, making it free from spatial restrictions.

Further, as the system takes a real image with the invisible light source which has no interference with visible light, the projected image on the subject may have high contrast. It further enables integration of a plurality of fluorescent imaging devices in one system so that a variety of augmented reality images can be provided.

Further, the augmented reality image projection system according to at least one embodiment can be built in a compact form so that it minimizes blocked line of sight or intervened movement of the operator, providing easier manipulation in various surgical operations.

Further, the augmented reality image projection system according to at least one embodiment can be built in a compact form so that it can be used in a narrow and confined operational site, or in a tight space such as an abdominal cavity when integrated directly into an eyepiece of a laparoscope, cystoscope, or thoracoscope.

Further, the augmented reality image projection system according to at least one embodiment can be built into a compact device so that multiples of the device can be installed in an astral lamp. In that case, a blocked projection image by the operators is well compensated by the remaining projection images to continue to offer clear object images. Integrating the projection system into the astral lamp also provide consistent, reliable projection as the astral lamp assumes the minimal intervention position regardless of the movements of surgeons.

DETAILED DESCRIPTION

A detailed description of an augmented reality image projection system according to some embodiments of the present disclosure is provided below.

Figure 1:
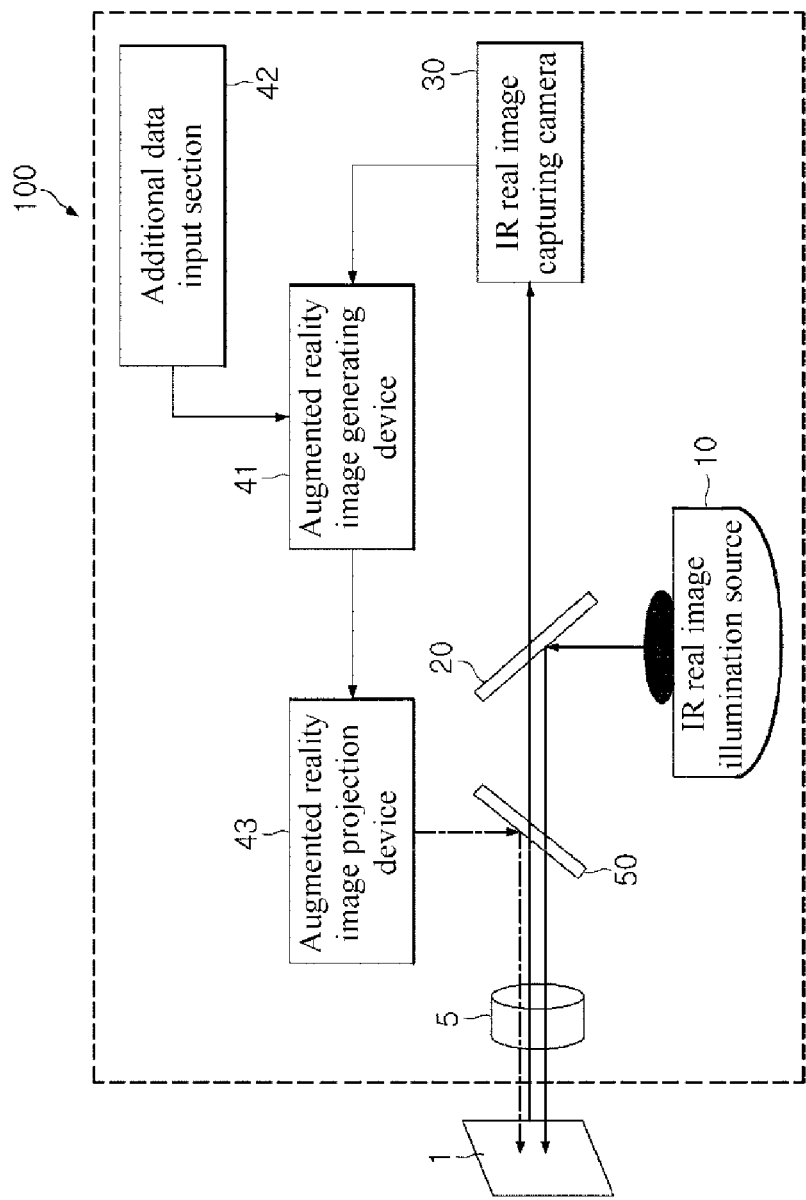
FIG. 1 is a schematic diagram of an augmented reality image projection system according to a first embodiment of the present disclosure.

FIG. 1 is a schematic diagram of a first embodiment of the augmented reality image projection system according to the present disclosure. The AR image projection system includes an IR (infrared) real image illumination source 10, a beam splitter 20, an IR real-image-capturing camera or simply IR real image camera 30, an AR (augmented reality) image generating device 41, an additional data input section 42, an AR image projection device 43, and a dichroic mirror 50.

The IR real image illumination source 10 provides illumination light for capturing a real image for the IR real image camera 30. In some embodiments, the IR real image illumination source 10 provides infrared illumination light having no interference with visible rays for enabling the AR image projection device 43 to project a contrasty AR image.

The beam splitter 20, which is a light deflection means, distributes an infrared ray by 50:50 ratio. The beam splitter 20 reflects the light rays from the IR real image illumination source 10 and passes the reflected ray of the real image for the IR real image camera 30 to capture.

Such combination of the IR real image illumination source 10 and the beam splitter 20 enables IR real image capturing without an interference with visible rays, and provides adjustment of the optical axis.

The real image taken by the IR real image camera 30 is transmitted to the AR image generating device 41, wherein additional location-based information in an image or text format may be added by the additional data input section 42 for the information to appear in the AR image.

The AR image generated by the AR image generating device 41 is transmitted to subject 1 through the AR image projection device 43 which transmits the AR image through the dichroic mirror 50 along a path collinear to the optical axis of the IR real image camera 30. The AR image projection device 43 further serves to illuminate the subject 1 in some embodiments.

The dichroic mirror 50 is located in between the AR image projection device 43 and the lens 5, and it serves as an image deflection means which totally reflects visible light and transmits light having a wavelength longer than the visible light.

The AR image projection system according to some embodiments is configured to have both the AR image projection device and the real image capture device to share the same optical axis. This obviates the need for an additional alignment device for aligning the AR image with the subject, and optically provides an AR image exactly rendered over the subject regardless of the shape of the subject or distance between the subject and the camera without a complicated calculation or the need for structural or functional devices such as a mixed set of infrared markers or a stereoscopic camera.

Figure 2:
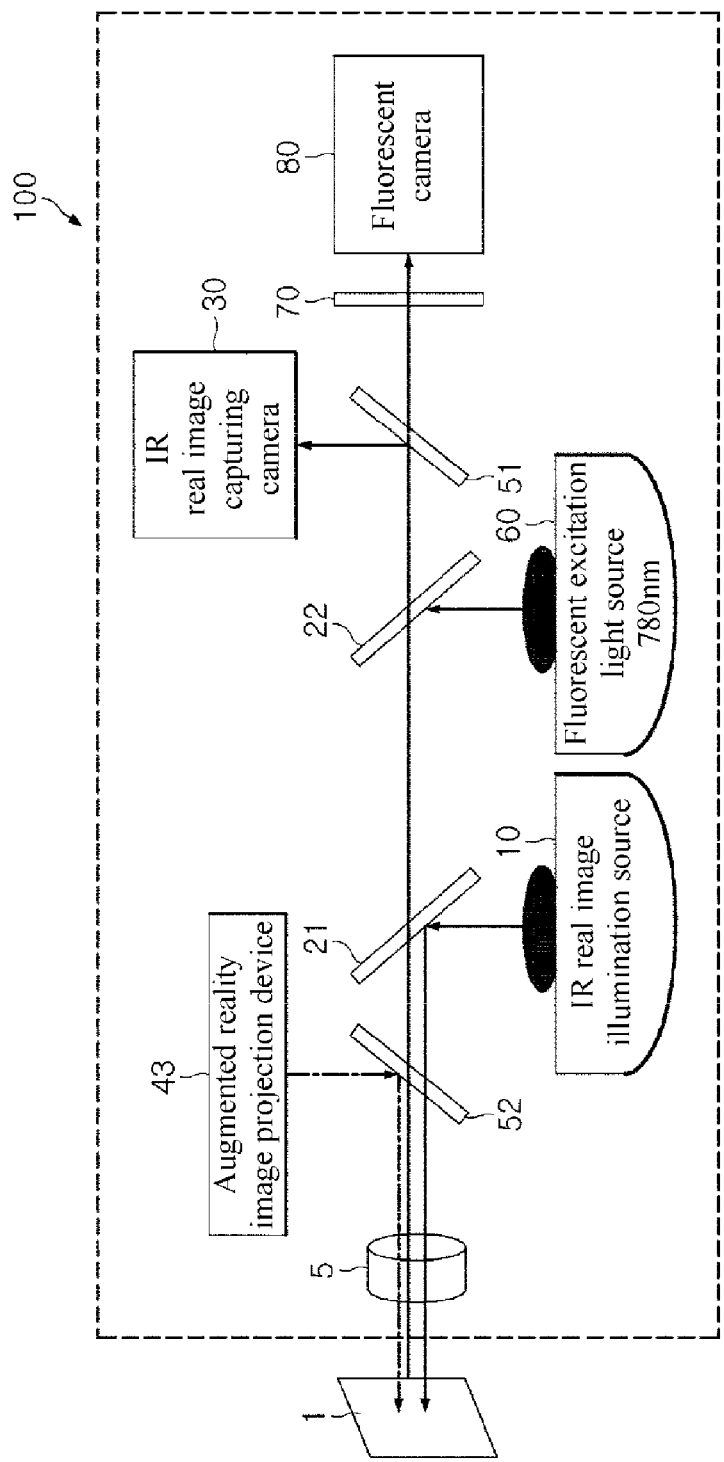
FIG. 2 is a schematic diagram of an augmented reality image projection system according to a second embodiment of the present disclosure.

FIG. 2 is a schematic diagram of a second embodiment of the AR image projection system among some embodiments of the present disclosure, including an IR real image illumination source 10, a first beam splitter 21, an IR real image camera 30, a first dichroic mirror 51, a fluorescent excitation light source 60, a second beam splitter 22, a fluorescent camera 80, a filter 70, an AR image projection device 43, and a second dichroic mirror 52.

This second embodiment according to the present disclosure shows an example case of adding a fluorescent image to a virtual image generated by the computer along with the same optical axis of the system. The specific forms and locations of the beam splitters and the dichroic mirrors may vary according to the wavelength of the fluorescence.

In the second embodiment according to the present disclosure, the fluorescent excitation light source 60 provides excitation light of 780 nm, then the second beam splitter 22 reflects the excitation light and transmits reflected incoming excitation light to the fluorescent camera 80 through the filter 70 to acquire a fluorescent image of 850 nm.

The fluorescent excitation light source may also be used as an illumination source for the real image. The second embodiment according to the present disclosure is described as having a single set of the fluorescent excitation light source 60 and the fluorescent camera 80, although it is not so limited. It is envisioned to have a plurality of sets of the same, which is further arranged with at least one dichroic mirror, at least one filter, and at least one fluorescent camera.

Figure 3C:
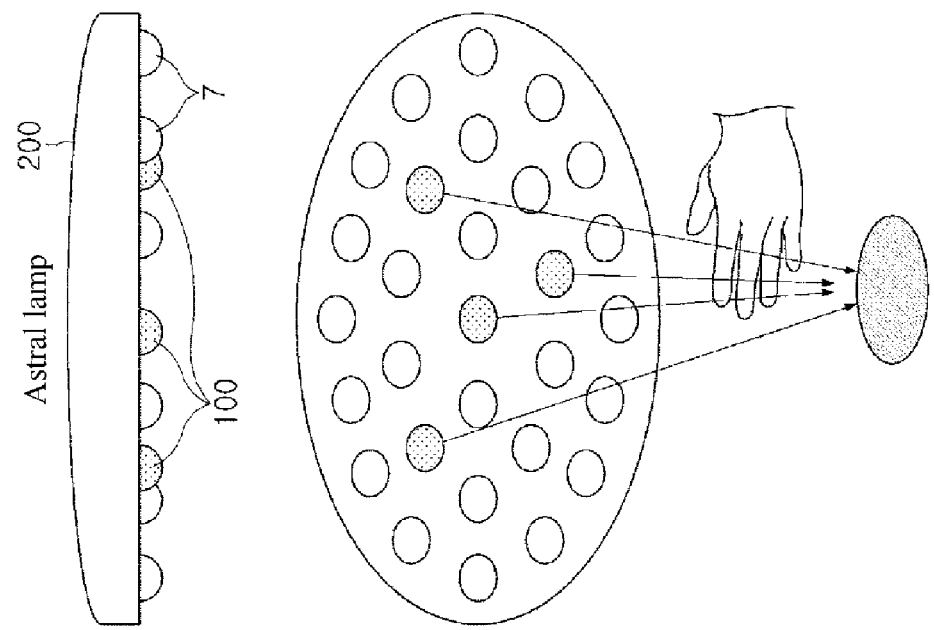
FIGS. 3A to 3C are schematic diagrams of an augmented reality image projection system according to some embodiments as applied to a) a laparoscope, b) a narrow area such as the surgical site and c) an astral lamp.
Figure 3A:
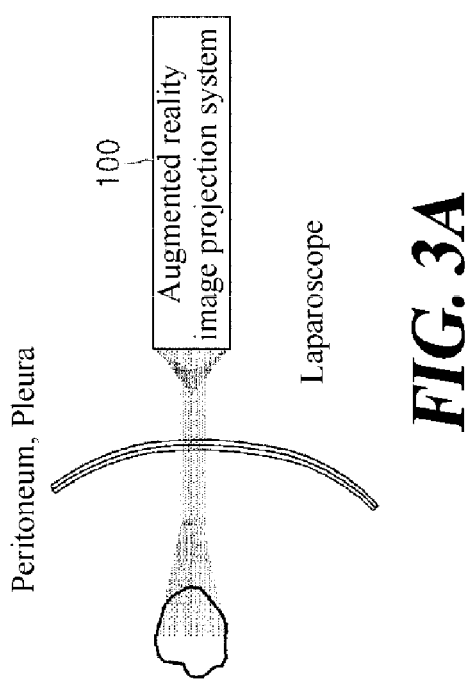
Figure 3B:
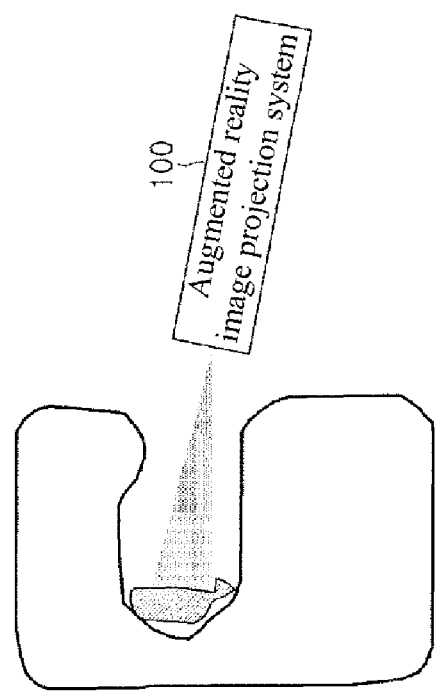
Figure 4:
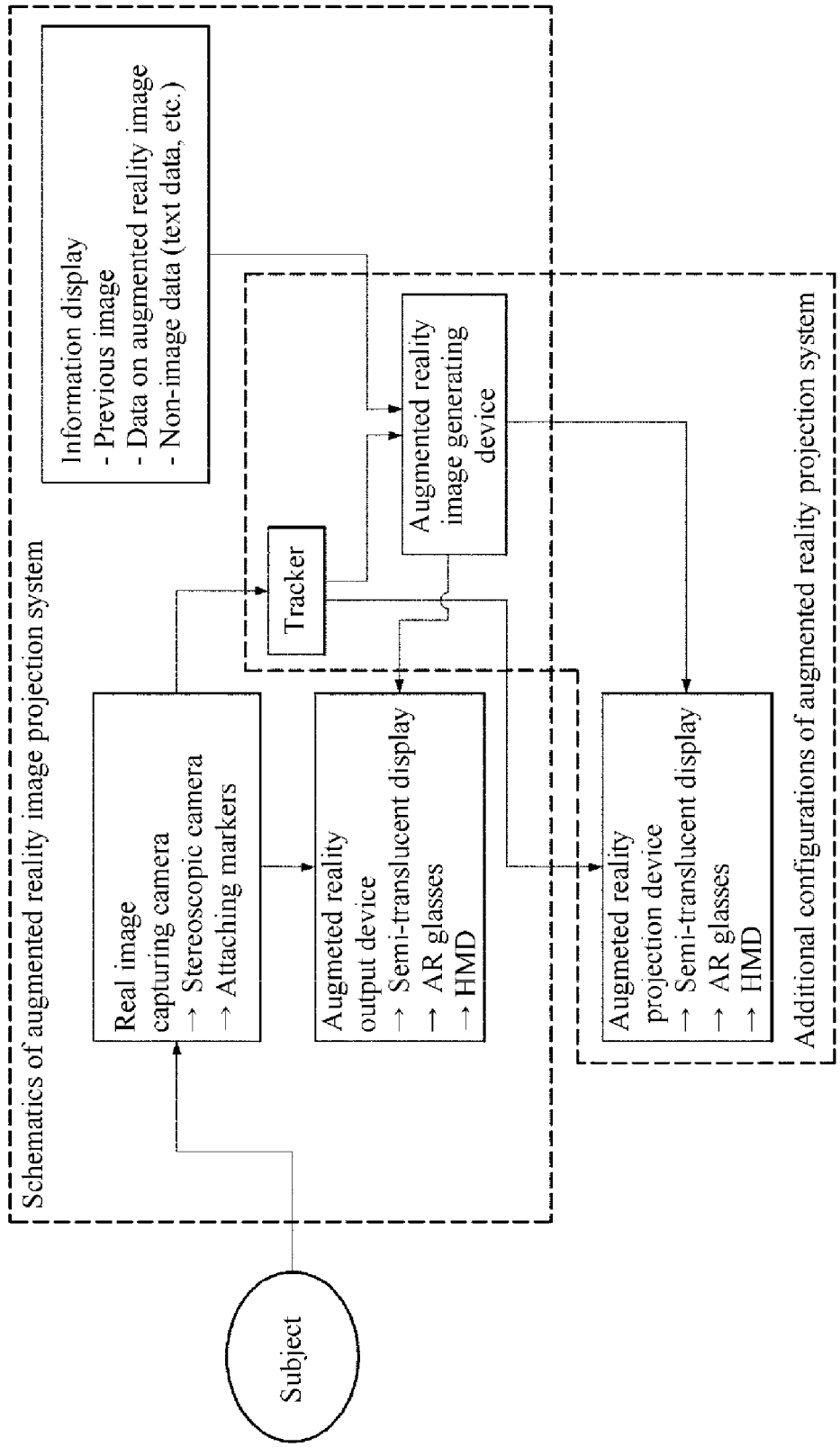
FIG. 4 is a schematic diagram showing an issue (such as blind spots) in a conventional augmented reality image projection system where the optical axes of the projection device and the imaging device are not concentric.
Figure 5:
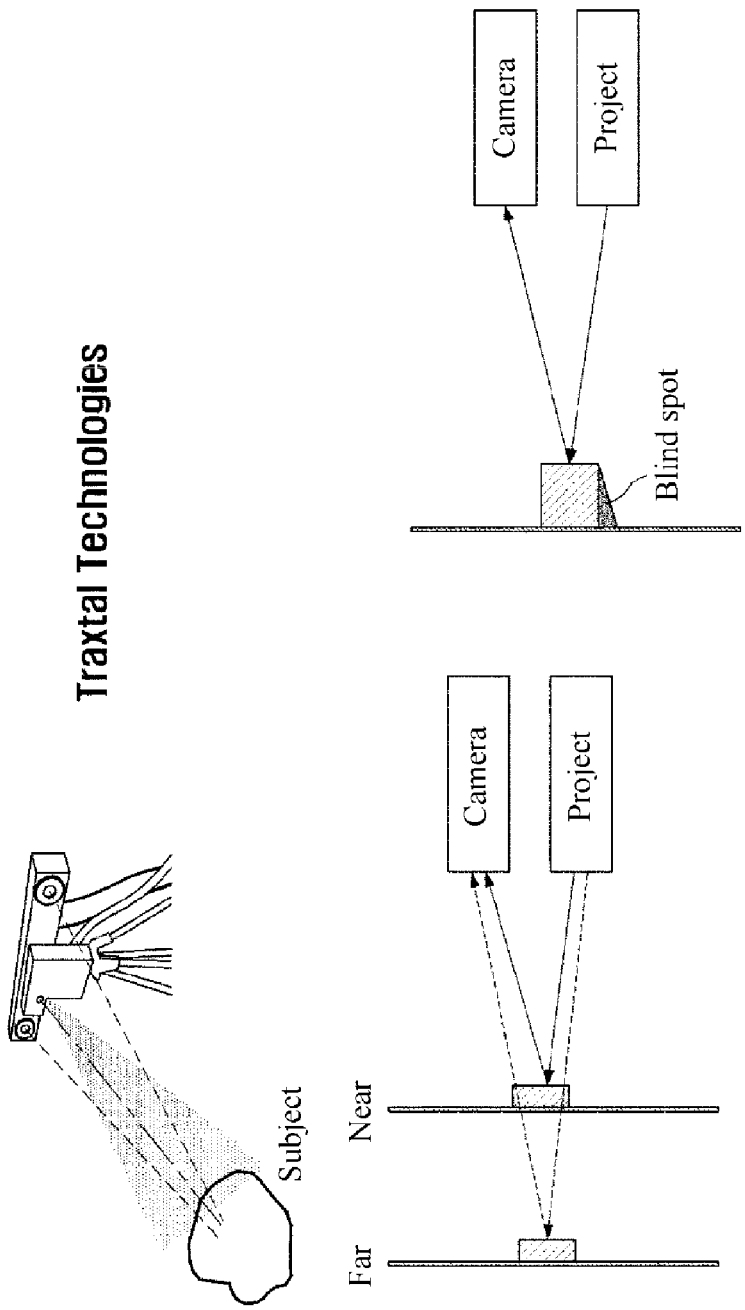
FIG. 5 is a schematic diagram of a conventional augmented reality system and a conventional augmented reality image projection system.

FIGS. 3A to 3C are schematic diagrams of the various embodiments of the AR image projection system according to the present disclosure. FIG. 3A is an embodiment for a laparoscope or thoracoscope. With a commercial rigid endoscope coupler lens used in place of the lens in some embodiments or with such lens modified into a form of rigid endoscope coupler lens, an AR image may be projected into an abdominal cavity or thoracic cavity without providing an additional device. In addition, the AR image projection system can be implemented as a miniaturized apparatus to project AR images on a subject located within a narrow and deep site as shown in FIG. 3B, if not the abdominal cavity or thoracic cavity. The AR image may be utilized effectively in surgery or manipulation as it provides maximum visibility for the user or the operator (surgeon).

FIG. 3C is an embodiment for an astral lamp. When implemented as a miniaturized apparatus, at least one AR image projection system may be installed in the astral lamp, to offer the capability of the AR image projection system conveniently in the operational site. In addition, having multiples of the AR image projection system 100 in the astral lamp 200 guarantees reliable projection of the AR images, overcoming shadowing by the operator or surgeon.

As described above, according to some embodiments of the present disclosure, the AR image projection system in application has the AR image projection device, the real image capturing device, and the fluorescent camera arranged to share the same optical axis, obviating the need to have an additional device for aligning the AR image to the subject or an extra device for aligning the computer-generated image to the real image. Thus, the AR image projection system can be made in simple, miniature form. The system according to some embodiments of the present disclosure may be used in a wide range of applications including operation, manipulation or laparoscopy.

In addition, the AR image projection system takes a real image with the infrared light source which has no interference with visible light, so as to provide the projected image on the subject with an enhanced contrast. With a plurality of fluorescent imaging devices integrated in the AR image projection system, a variety of AR images can be provided.

While particular embodiments of the present disclosure have been shown and described, it will be obvious to those skilled in the art that, based upon the teachings herein, changes and modifications may be made from the AR image projection system without departing from the technical ideas of this disclosure.

The invention claimed is:

1. An augmented reality image projection system, comprising:
   a real image capture device configured to take a real image of a subject; and
   an augmented reality image projection device configured to project an augmented reality image onto the subject, wherein the real image capture device comprises an IR (infrared) real image capture device capable of capturing an infrared image, and the augmented reality image projection system further comprises an IR real image illumination source which provides infrared light for the IR real image capture device to capture the real image and a beam splitter configured to distribute the infrared light provided by the IR real image illumination source, and
   wherein through the same projection lens and along the same optical axis, the real image is captured and the augmented reality image is projected.

2. The augmented reality image projection system of claim 1, further comprising:
   a first dichroic mirror configured
      to be disposed between the augmented reality image projection device and the projection lens, and
      to totally reflect the visible light while passing light having a wavelength longer than the visible light.

3. The augmented reality image projection system of claim 2, wherein the real image capture device and the augmented reality image projection device are incorporated at least in an astral lamp or in an eyepiece of at least one rigid endoscope of a laparoscope, a thoracoscope, or a cystoscope.

4. The augmented reality image projection system of claim 1, wherein the real image capture device and the augmented reality image projection device share the same optical axis, and the augmented reality image projection system further comprises a fluorescent camera configured to take a fluorescent image.

5. The augmented reality image projection system of claim 4, further comprising:
   a fluorescent excitation light source configured to provide an excitation light for the fluorescent camera to take the fluorescent image.

6. The augmented reality image projection system of claim 5, further comprising:
   a second dichroic mirror configured to reflect a particular wavelength of the excitation light from the fluorescent excitation light source while passing other wavelength than the particular wavelength of the excitation light.

7. The augmented reality image projection system of claim 6, wherein the real image capture device and the augmented reality image projection device are incorporated at least in an astral lamp or in an eyepiece of at least one rigid endoscope of a laparoscope, a thoracoscope, or a cystoscope.

8. The augmented reality image projection system of claim 5, wherein the real image capture device and the augmented reality image projection device are incorporated at least in an astral lamp or in an eyepiece of at least one rigid endoscope of a laparoscope, a thoracoscope, or a cystoscope.

9. The augmented reality image projection system of claim 4, further comprising:
   a filter configured to be disposed in front of the fluorescent camera and to filter an excitation light for taking the fluorescent image.

10. The augmented reality image projection system of claim 9, wherein the real image capture device and the augmented reality image projection device are incorporated at least in an astral lamp or in an eyepiece of at least one rigid endoscope of a laparoscope, a thoracoscope, or a cystoscope.

11. The augmented reality image projection system of claim 4, wherein the real image capture device and the augmented reality image projection device are incorporated at least in an astral lamp or in an eyepiece of at least one rigid endoscope of a laparoscope, a thoracoscope, or a cystoscope.

12. The augmented reality image projection system of claim 1, wherein the real image capture device and the augmented reality image projection device are incorporated at least in an astral lamp or in an eyepiece of at least one rigid endoscope of a laparoscope, a thoracoscope, or a cystoscope.

13. The augmented reality image projection system of claim 1,
   wherein the beam splitter distributes the infrared light provided by the IR real image illumination source by 50:50 ratio.

14. The augmented reality image projection system of claim 13, wherein the real image capture device and the augmented reality image projection device are incorporated at least in an astral lamp or in an eyepiece of at least one rigid endoscope of a laparoscope, a thoracoscope, or a cystoscope.

* * * * *